(12) United States Patent
Hector

(10) Patent No.: US 7,305,267 B2
(45) Date of Patent: Dec. 4, 2007

(54) CONNECTOR MODULE HAVING REDUCED INSERTION FORCE

(75) Inventor: Wayne M. Hector, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 385 days.

(21) Appl. No.: 10/767,152

(22) Filed: Jan. 29, 2004

(65) Prior Publication Data
US 2005/0171509 A1    Aug. 4, 2005

(51) Int. Cl.
A61N 1/375    (2006.01)

(52) U.S. Cl. .............. 607/37; 607/9; 607/36; 607/38; 604/9; 439/909

(58) Field of Classification Search ........... 607/36–38, 607/9; 604/9; 439/909; 907/9
See application file for complete search history.

(56) References Cited

U.S. PATENT DOCUMENTS

| 4,262,673 | A | * | 4/1981 | Kinney et al. ................. 607/5 |
| 4,301,805 | A | * | 11/1981 | Peers-Trevarton et al. .... 607/37 |
| 4,316,471 | A | | 2/1982 | Shipko et al. |
| 4,934,366 | A | * | 6/1990 | Truex et al. ................... 607/37 |
| 6,039,685 | A | | 3/2000 | Bushek |
| 2004/0215282 | A1 | * | 10/2004 | Weijden et al. ............... 607/37 |
| 2005/0131481 | A1 | * | 6/2005 | Ries et al. .................... 607/36 |

* cited by examiner

*Primary Examiner*—Carl Layno
*Assistant Examiner*—Shevon E Johnson
(74) *Attorney, Agent, or Firm*—Carol F. Barry; Steve Bauer

(57) ABSTRACT

A medical device connector module includes a lead retention element extending through an opening in a sidewall of the connector module. The retention element includes a flow passage in fluid communication with a connector bore of the connector module and an outer surface of the sidewall.

16 Claims, 5 Drawing Sheets

CONNECTOR MODULE HAVING REDUCED INSERTION FORCE

TECHNICAL FIELD

The present invention generally relates to medical devices, and in particular to a device connector module assembly.

BACKGROUND

Implantable medical devices (IMDs) typically include connector modules for the coupling of implantable medical leads to the devices; the medical leads include elongated bodies extending from a proximal connector and carrying conductors for delivery of therapy from the IMD to a selected site within a body of a patient. One type of therapy most commonly delivered through such leads is electrical stimulation therapy; therefore electrical contacts are formed on the lead connector to make electrical connection, within the connector module, between the conductors of the lead and the IMD. It should be noted that leads and devices may also be implanted solely for the purpose of diagnostic monitoring, wherein electrical contacts are also elements of the lead connector, or for the purpose of therapeutic agent infusion, wherein electrical contacts are not required elements. For the purposes of this application, reference will be made only to a pacemaker IMD and lead, it being understood that the principles herein may have applicability to a host of other medical systems.

Once a cardiac lead has been implanted such that one or more electrodes are in contact with cardiac tissue, the connector of the lead is inserted into an IMD connector module bore containing one or more electrical connectors that are configured to engage with one or more contacts located on the lead connector. Both electrical and fluid tight seals are required between each electrical contact and between the lead connector, within the bore, and the implant environment outside the bore. Sealing rings, mounted either on the lead connector or within the bore, create such seals, however it has been found that the seals may make full insertion of the lead connector difficult due to pressure build-up within the bore once a first set of sealing rings engages between the lead connector and the bore. Accordingly, there is a need for a device connector module assembly that relieves or vents this pressure.

BRIEF DESCRIPTION OF THE DRAWINGS

The following drawings are illustrative of particular embodiments of the invention and therefore do not limit the scope of the invention, but are presented to assist in providing a proper understanding. The drawings are not to scale (unless so stated) and are intended for use in conjunction with the explanations in the following detailed description. The present invention will hereinafter be described in conjunction with the appended drawings, wherein like numerals denote like elements, and.

DETAILED DESCRIPTION

The following detailed description of the invention is merely exemplary in nature and is not intended to limit the scope, applicability, or configuration of the invention in any way. Rather, the following description provides a convenient illustration for implementing exemplary embodiments of the invention. Various changes to the described embodiments may be made in the function and arrangement of the elements described herein without departing from the scope of the invention.

Figure 1:
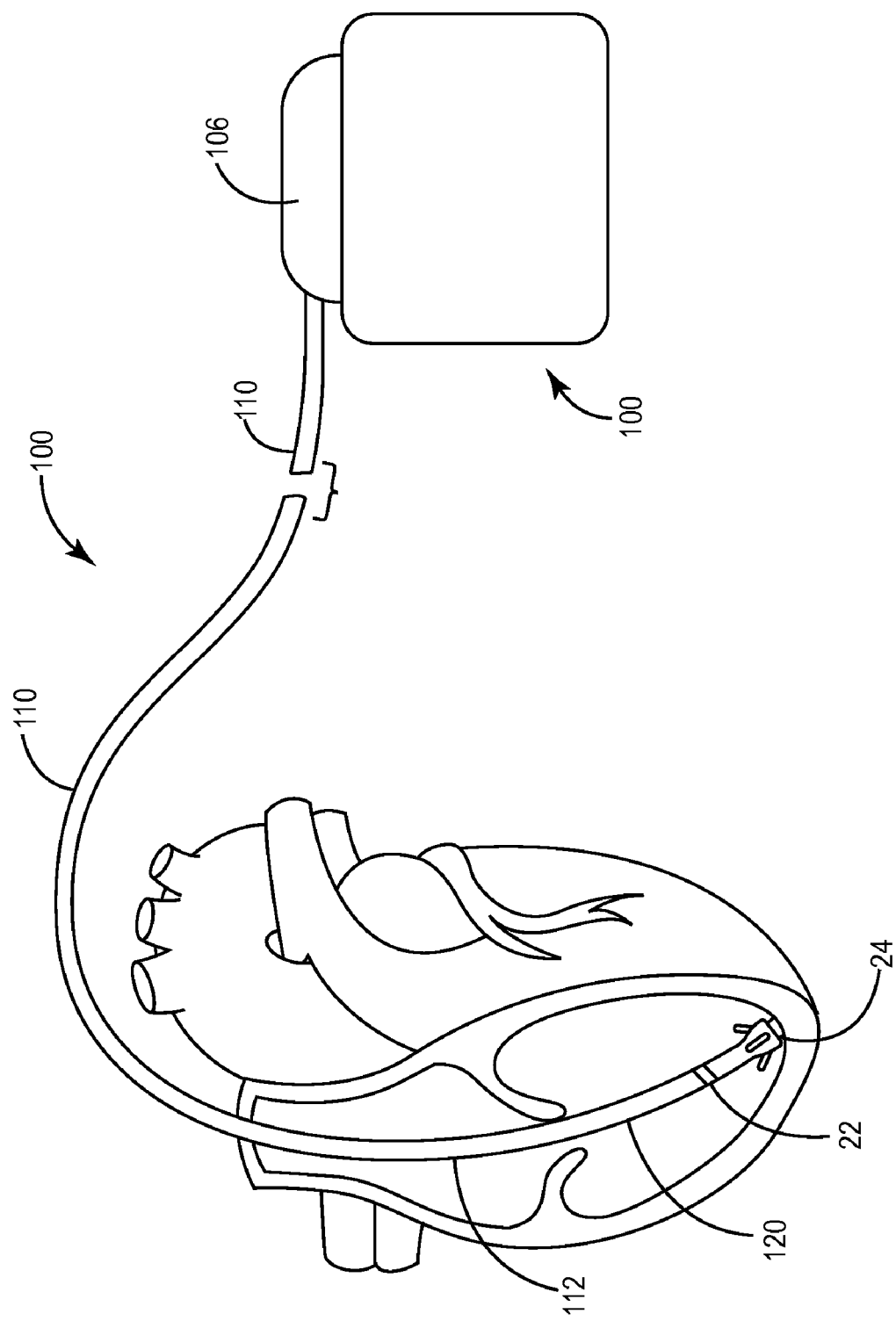
FIG. 1 is a schematic view of an exemplary medical system in which embodiments of the current invention may be incorporated.

FIG. 1 is a schematic view of an exemplary medical system in which embodiments of the current invention may be incorporated. FIG. 1 illustrates an IMD 100 including a connector module 106 from which an implantable lead 108 extends; implantable lead 108 includes an elongated lead body 110 including a distal portion 112 to which a pair of pace/sense electrodes 22, 24 are coupled. A proximal end of lead 108 is plugged into connector module 106 in order to couple electrodes 22, 24 to IMD 100 in a manner well known to those skilled in the art. Insulated conductors (not shown) extend within lead body 110 from electrodes 22 and 24 to a connector 107 terminating a proximal end of lead body 110, as illustrated in FIGS. 2A-B; the conductors couple electrodes 22 and 24 to connector ring 54 and connector pin 50, respectively.

Figure 2A:
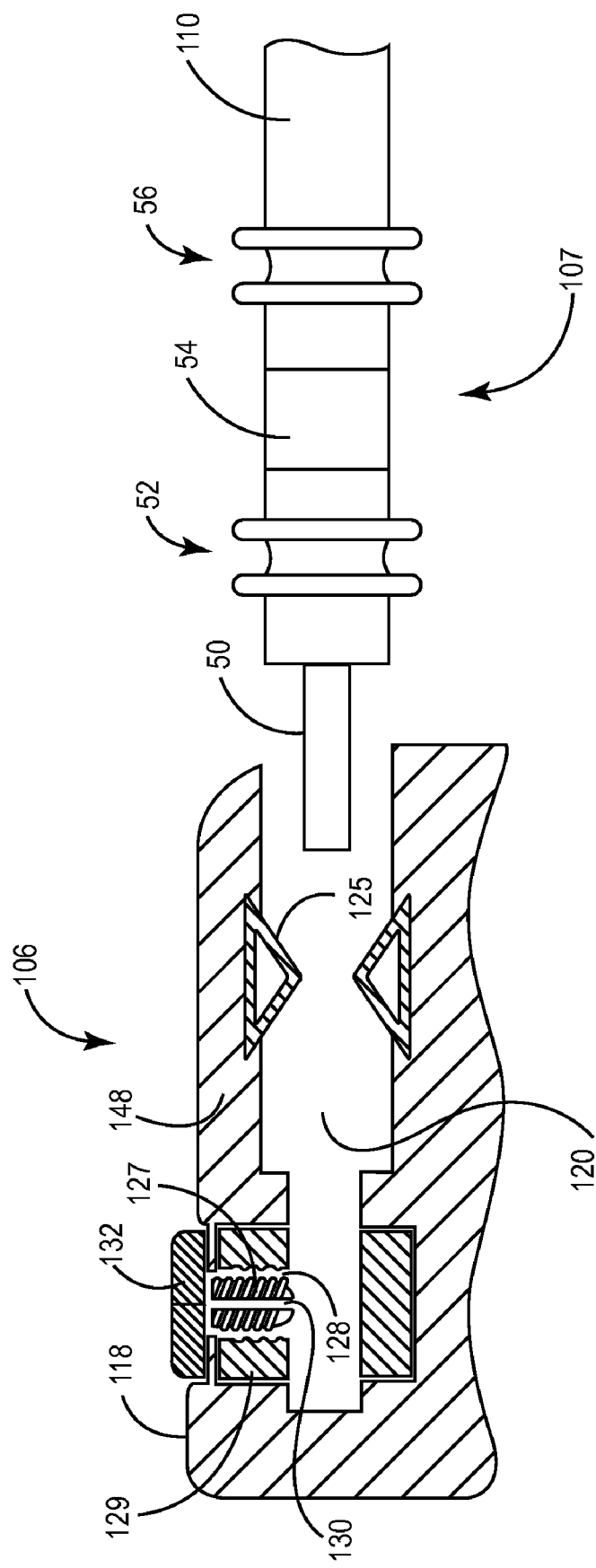
FIGS. 2A and 2B are plan views with partial section of embodiments according to the present invention.
Figure 2B:
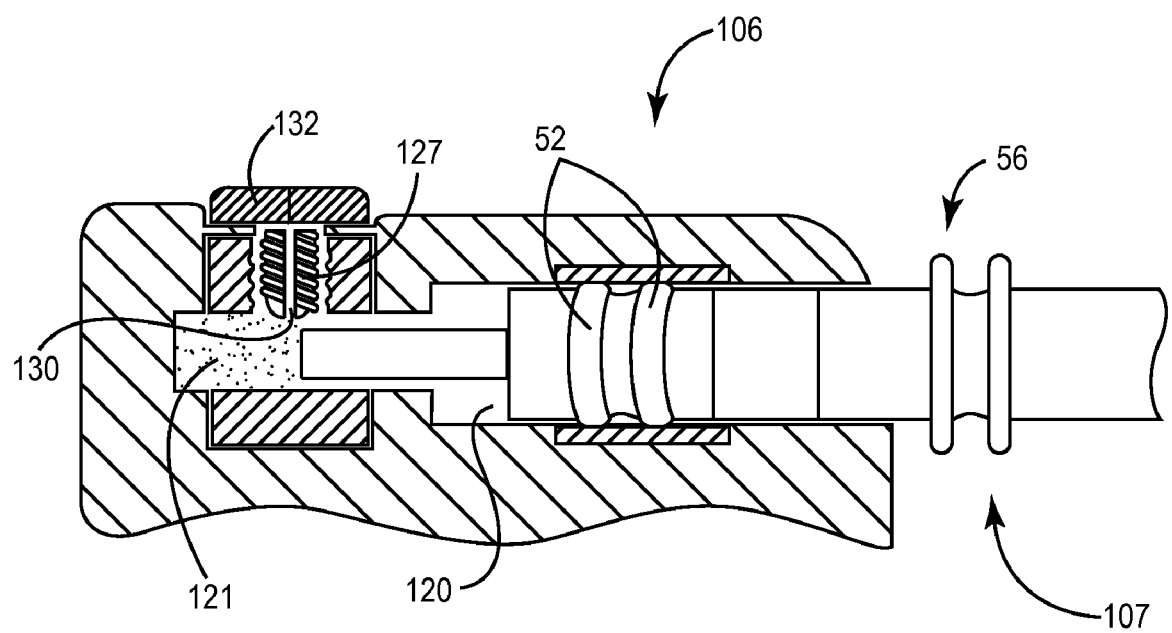

FIGS. 2A and 2B are plan views with partial section of embodiments according to the present invention. FIGS. 2A-B illustrate lead connector 107 further including a first set of sealing rings 52 and a second set of sealing rings 56 adapted to provide electrical isolation and a fluid tight seal for connector 107 inserted within bore 120. FIGS. 2A-B further illustrate connector module 106 including a sidewall 148 forming an outer surface 118 and a connector bore 120 into which lead connector 107 is to be inserted such that a contact 125 engages connector ring 54 and a set-screw 127 in combination with a threaded connector block 129 engages connector pin 50. Contact 125 is illustrated as a multi-beam spring contact but may take any other form known to those skilled in the art. Set-screw 127 and connector block 129 form both a means of electrical engagement and a means of secure retention when engaging pin 50, wherein set-screw 127 is fastened down on pin 50 though an opening 128 in sidewall 148.

According to embodiments of the present invention set-screw 127 includes a flow passage 130, in fluid communication with bore 120 and outer surface 118 of sidewall 148, through which fluid pressure may be relieved when connector 107 is inserted into bore 120. As is illustrated in FIG. 2B once a first set of connector sealing rings 52 becomes engaged within bore 120, air is compressed into a distal end 121 of bore 120; flow passage 130 of set-screw 127 allows the air to escape from bore, thus relieving a pressure build up which could inhibit full insertion of connector 107. It should be noted that, in an alternate embodiment according to the present invention, connector 107 does not include sealing ring sets 52 and 56 while bore 120 includes inwardly extending sealing rings adapted to sealingly engage surfaces of connector 107 on either side of connector ring 54.

Figure 2C:
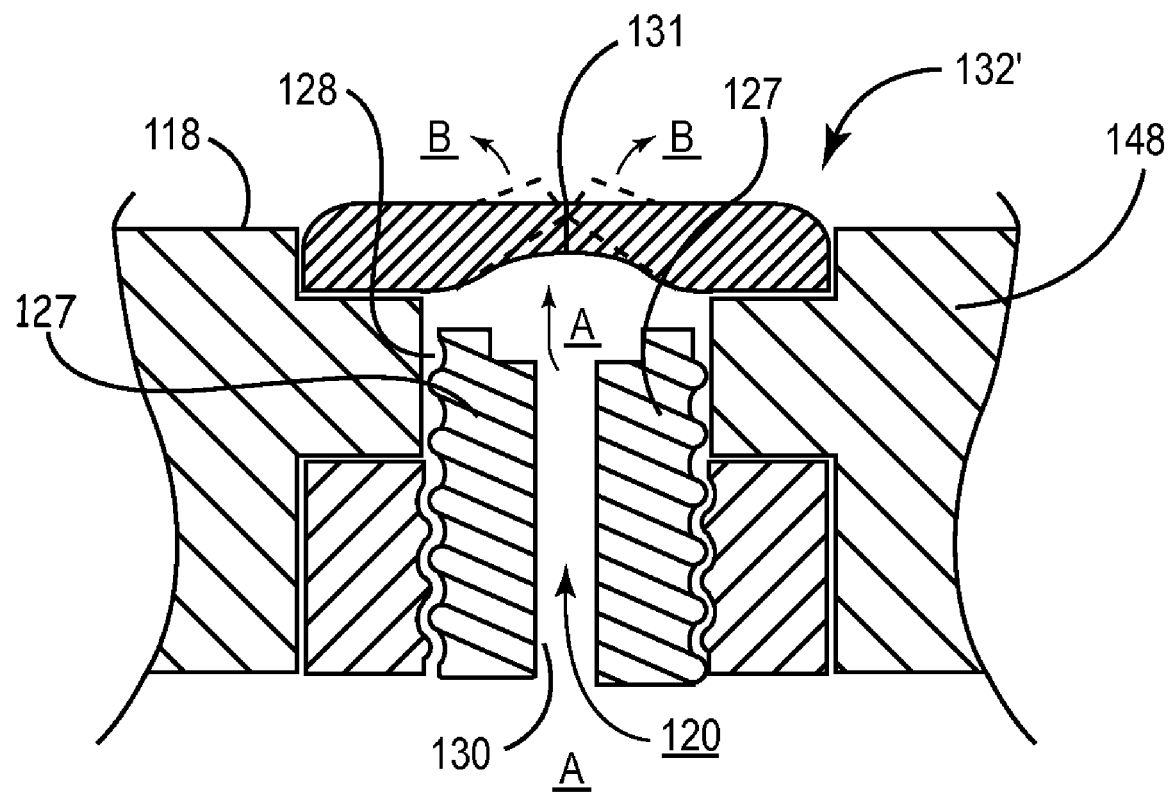
FIG. 2C is an enlarged section detail from FIG. 2B of one embodiment.

FIGS. 2A-B further illustrate a grommet seal 132 positioned over set-screw 127 to prevent fluid ingression into bore after connector 107 is fully inserted into bore 107 and IMD 100 is implanted. According to one embodiment grommet 132 is positioned, as illustrated, and bonded in place after connector 107 has been fully inserted into bore 120; according to alternate embodiments grommet 132 is bonded into position over set-screw 127 prior to insertion of connector 107. One of these alternate embodiments is illustrated in FIG. 2C. FIG. 2C illustrates a grommet 132', which is adapted to open, per arrows B, in response to an internal pressure, created by connector 107 insertion (FIG. 2B), that drives a fluid from bore 120 out through flow passage 130, per arrows A.

Figure 3:
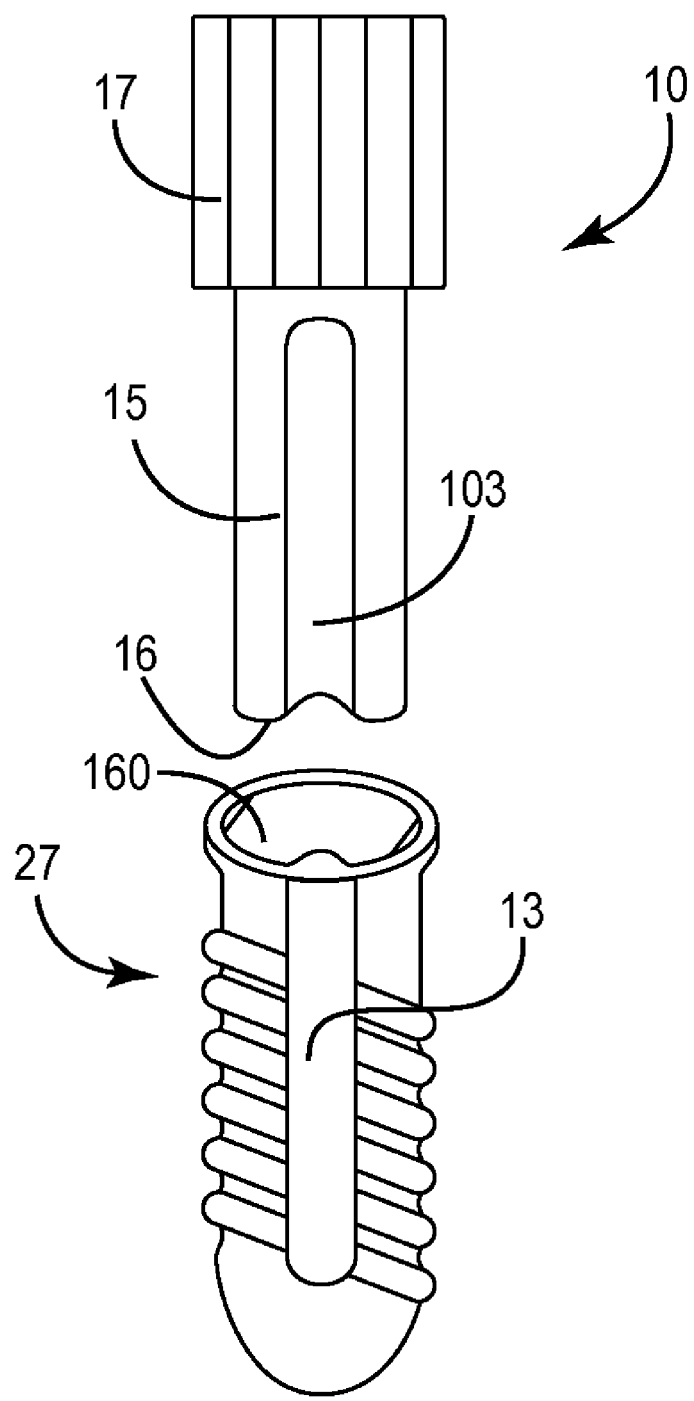
FIG. 3 is a perspective view of a portion of an alternate embodiment according to the present invention.

FIG. 3 is a perspective view of a portion of another alternate embodiment according to the present invention. FIG. 3 illustrates a fastening tool 10 including a handle or knob 17 and a shaft 15 extending therefrom; a distal end 16 of shaft 15 is adapted to engage an upper surface 160 of a set-screw 27, which may be interchanged with setscrew 127 illustrated in FIGS. 2A-2C. Set-screw 27, as shown, includes a flow passage 13 formed as a groove in an outer surface and tool 10 includes a flow passage 103, formed in an outer surface of shaft 15, which is adapted to be aligned with passage 13 of set-screw 27 when mated therewith. According to the illustrated embodiment, shaft 15 of tool 10 would be directed through a grommet seal, i.e. grommet 132 (FIGS. 2A-B), to engage set-screw 27 prior to connector insertion, thus, during connector insertion, flow passages 13 and 103 provide fluid communication between bore 120 and outer surface 118 in order to vent bore 120. After connector 107 is fully inserted into bore 120, tool 17 is rotated to fasten screw 27 down on pin 50 and removed back through grommet 132, which maintains a fluid tight seal thereafter.

While specific embodiments have been presented in the foregoing detailed description of the invention, it should be clear that a vast number of variations exist. It should also be appreciated that the exemplary embodiments are only examples, and are not intended to limit the scope, applicability, or configuration of the invention in any way. Rather, the foregoing detailed description will provide those skilled in the art with a convenient road-map for implementing an exemplary embodiment of the invention. It should be understood that various changes may be made in the function and arrangement of elements described in an exemplary embodiments without departing from the scope of the invention as set forth in the appended claims.

What is claimed is:

1. A medical device comprising:
a connector module having a connector bore adapted to receive a connector contact terminal of a medical electrical lead and including a sidewall forming an outer surface exposed to ambient conditions, the sidewall having an opening extending through the sidewall in a substantially orthogonal orientation to the connector bore; and a lead retention element extending through the orthogonal opening in the sidewall of the connector module, the retention element having a body portion with a tool engagement portion at one end and a connector contact engagement portion at the opposite end, the retention element body including a flow passage extending between the tool engagement portion and the connector contact engagement portion that establishes fluid communication between the connector bore and the outer surface of the sidewall so as to vent the connector bore to the ambient conditions outside the outer surface of the sidewall during insertion of the connector contact terminal into the connector module bore.

2. The device of claim 1, further comprising a seal formed over the retention element on the outer surface of the sidewall, the seal adapted to prevent ingress of fluids into the connector bore.

3. The device of claim 2, wherein the seal is further adapted to allow egress of fluid out from the bore when the medical lead is inserted into the bore.

4. The device of claim 1, wherein the retention element comprises a set-screw.

5. The device of claim 4, wherein the flow passage is formed as a bore extending longitudinally through the set-screw.

6. The device of claim 4, wherein the flow passage is formed as groove extending longitudinally along an outer surface of the set-screw.

7. A medical device comprising:
a connector module including a sidewall forming an outer surface and a connector bore adapted to engage a medical lead;
a lead retention element extending through an opening in the sidewall of the connector module, the retention element including a flow passage in fluid communication with the connector bore and the outer surface of the sidewall,
a seal formed over the retention element on the outer surface of the sidewall, the seal adapted to prevent ingress of fluids into the connector bore; and
a tool adapted to engage the retention element through the seal, the tool including a flow passage which is in fluid communication with the retention element flow passage and with an outer surface of the seal when the tool is engaged with the retention element.

8. The device of claim 4, wherein the retention element comprises a set-screw and the flow passage is formed as a groove extending longitudinally along an outer surface of the set-screw.

9. A method for venting a connector module bore of a medical device, the method comprising the steps of:
inserting a tool through a seal formed over a retention element of the connector module; and
engaging the retention element with the tool such that a flow passage formed in the tool is aligned with a flow passage formed in the retention element to provide fluid communication between the connector module bore and an outer surface of the seal.

10. A medical device connector module, comprising:
a sidewall forming an outer surface;
a connector bore adapted to engage a medical lead;
the sidewall being exposed to ambient conditions, and having an opening extending through the sidewall in a substantially orthogonal orientation to the connector bore; and
a lead retention element extending through the opening in the sidewall, the retention element having a body portion with a tool engagement portion at one end and a connector contact engagement portion at the opposite end, the retention element body including a flow passage extending between the tool engagement portion and the connector contact engagement portion that establishes fluid communication between the connector bore and the outer surface of the sidewall so as to vent the connector bore to the ambient conditions outside the outer surface of the sidewall during insertion of the connector contact terminal into the connector module bore.

11. The connector module of claim 10, further comprising a seal formed over the retention element on the outer surface of the sidewall, the seal adapted to prevent ingress of fluids into the connector bore.

12. The connector module of claim 11, wherein the seal is further adapted to allow egress of fluid out from the bore when the medical lead is inserted into the bore.

13. The connector module of claim 10, wherein the retention element comprises a set-screw.

14. The connector module of claim 13, wherein the flow passage is formed as a bore extending longitudinally through the set-screw.

15. The connector module of claim 13, wherein the flow passage is formed as groove extending longitudinally along an outer surface of the set-screw.

16. A medical device connector module, comprising:
a sidewall forming an outer surface;
a connector bore adapted to engage a medical lead;
a lead retention element extending through an opening in the sidewall, the retention element including a flow passage in fluid communication with the connector bore and the outer surface of the sidewall; and
a tool adapted to engage the retention element, the tool including a flow passage which is in fluid communication with the retention element flow passage when the tool is engaged with the retention element.

* * * * *

UNITED STATES PATENT AND TRADEMARK OFFICE
CERTIFICATE OF CORRECTION

PATENT NO. : 7,305,267 B2
APPLICATION NO. : 10/767152
DATED : December 4, 2007
INVENTOR(S) : Wayne Hector Page 1 of 1

It is certified that error appears in the above-identified patent and that said Letters Patent is hereby corrected as shown below:

Col. 4, line 46, delete "claim 4" and insert in place there of --claim 5--.

Signed and Sealed this

Sixth Day of January, 2009

JON W. DUDAS
*Director of the United States Patent and Trademark Office*